(12) United States Patent
Haddad et al.

(10) Patent No.: US 9,249,313 B2
(45) Date of Patent: Feb. 2, 2016

(54) SYNTHESIS OF FUNCTIONAL FLUORINATED POLYHEDRAL OLIGOMERIC SILSESQUIOXANE (F-POSS)

(71) Applicants: Timothy S. Haddad, Lancaster, CA (US); Joseph M. Mabry, Lancaster, CA (US); Sean Ramirez, Lancaster, CA (US)

(72) Inventors: Timothy S. Haddad, Lancaster, CA (US); Joseph M. Mabry, Lancaster, CA (US); Sean Ramirez, Lancaster, CA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 13/624,151

(22) Filed: Sep. 21, 2012

(65) Prior Publication Data
US 2013/0072609 A1  Mar. 21, 2013

Related U.S. Application Data

(60) Provisional application No. 61/537,122, filed on Sep. 21, 2011.

(51) Int. Cl.
| | | |
|---|---|---|
| C07F 7/21 | (2006.01) | |
| B05D 3/12 | (2006.01) | |
| C08K 5/549 | (2006.01) | |

(Continued)

(52) U.S. Cl.
CPC ............. *C09D 5/1662* (2013.01); *C07F 7/21* (2013.01); *B05D 5/083* (2013.01)

(58) Field of Classification Search
USPC ............................ 524/261; 556/460; 427/240
See application file for complete search history.

(56) References Cited

U.S. PATENT DOCUMENTS

| | | | |
|---|---|---|---|
| 2,687,424 A | 8/1954 | Sommer | |
| 3,382,279 A | 5/1968 | Hans Niederprum | |

(Continued)

FOREIGN PATENT DOCUMENTS

| | | |
|---|---|---|
| CN | 102659827 | 9/2012 |

OTHER PUBLICATIONS

F. J. Feher et al., "A new route to heterosilsesquioxane frameworks," Angew. Chem., Int. Ed. vol. 37 (1998) 2663-2667.

(Continued)

*Primary Examiner* — Peter D Mulcahy
*Assistant Examiner* — Henry Hu
(74) *Attorney, Agent, or Firm* — AFMCLO/JAZ; Chastity Whitaker

(57) ABSTRACT

A functional fluorinated polyhedral oligomeric silsesquioxane ("F-POSS"). The F-POSS, has a chemical structure:

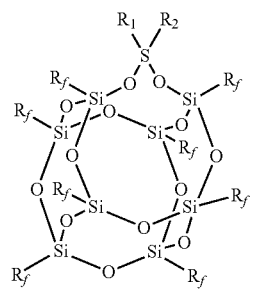

where $R_f$ represents a nonreactive organic group and at least one of $R_1$ and $R_2$ represents a chain comprising at least three carbon atoms.

12 Claims, 7 Drawing Sheets

(51) Int. Cl.
  *C09D 5/16* (2006.01)
  *B05D 5/08* (2006.01)

(56) References Cited

U.S. PATENT DOCUMENTS

| | | | |
|---|---|---|---|
| 3,465,017 | A | 9/1969 | Coutant |
| 4,709,008 | A | 11/1987 | Shimp |
| 4,774,028 | A | 9/1988 | Imai et al. |
| 5,258,534 | A | 11/1993 | Larson et al. |
| 5,283,348 | A | 2/1994 | Bank |
| 5,284,968 | A | 2/1994 | Craig, Jr. |
| 5,629,394 | A | 5/1997 | Cheradame et al. |
| 5,912,377 | A | 6/1999 | Hall et al. |
| 6,057,402 | A | 5/2000 | Zhou et al. |
| 6,217,943 | B1 | 4/2001 | Hall et al. |
| 6,489,380 | B1 | 12/2002 | Zhou et al. |
| 6,716,919 | B2 | 4/2004 | Lichtenhan et al. |
| 6,767,930 | B1 | 7/2004 | Svejda |
| 6,770,724 | B1* | 8/2004 | Lichtenhan et al. ............ 528/14 |
| 6,844,379 | B2 | 1/2005 | Zhou et al. |
| 6,911,518 | B2 | 6/2005 | Lichtenhan |
| 7,053,167 | B2* | 5/2006 | Ito et al. ......................... 528/31 |
| 7,157,117 | B2 | 1/2007 | Mikhael |
| 7,193,015 | B1 | 3/2007 | Mabry et al. |
| 7,291,747 | B2 | 11/2007 | Oikawa et al. |
| 7,332,822 | B2 | 2/2008 | Basheer |
| 7,790,841 | B1 | 9/2010 | Yandek et al. |
| 7,897,667 | B2 | 3/2011 | Mabry et al. |
| 8,058,380 | B1 | 11/2011 | Vij et al. |
| 8,276,664 | B2* | 10/2012 | Gupta ..................... C08B 1/003 166/278 |
| 8,557,329 | B2 | 10/2013 | Dai et al. |
| 8,565,892 | B2 | 10/2013 | Nayfach-Battilana |
| 8,580,027 | B1 | 11/2013 | Campos et al. |
| 8,741,432 | B1 | 6/2014 | Campos et al. |
| 9,052,653 | B2 | 6/2015 | Moorlag |
| 2001/0016616 | A1 | 8/2001 | Yeager et al. |
| 2004/0067339 | A1 | 4/2004 | Gandon |
| 2005/0009982 | A1 | 1/2005 | Inagaki et al. |
| 2006/0194068 | A1 | 8/2006 | Katoh et al. |
| 2006/0286555 | A1 | 12/2006 | Van Beuningen |
| 2007/0173657 | A1 | 7/2007 | Chen et al. |
| 2008/0199805 | A1 | 8/2008 | Ruskin |
| 2009/0069508 | A1 | 3/2009 | Poe |
| 2009/0176097 | A1 | 7/2009 | Brown et al. |
| 2010/0063244 | A1 | 3/2010 | Poe |
| 2010/0068168 | A1 | 3/2010 | Song |
| 2010/0098761 | A1 | 4/2010 | Song |
| 2010/0159011 | A1 | 6/2010 | Lian |
| 2010/0280561 | A1 | 11/2010 | Song |
| 2010/0316842 | A1 | 12/2010 | Tuteja et al. |
| 2011/0229706 | A1 | 9/2011 | Epstein |
| 2011/0283778 | A1 | 11/2011 | Angelescu |
| 2012/0000853 | A1* | 1/2012 | Tuteja et al. .................. 210/650 |
| 2012/0015191 | A1 | 1/2012 | Treadway |
| 2012/0190532 | A1 | 7/2012 | Celiker et al. |
| 2012/0214269 | A1 | 8/2012 | Harding |

OTHER PUBLICATIONS

F. J. Feher et al., "A new route to incompletely-condensed silsesquioxanes: acid-mediated cleavage and rearrangement of (c-C6H11)6Si6O9 to C2-[(c-C6H11)6Si6O8X2]," Chem. Commun. (1999) 1705-1706.
F. J. Feher et al., "A new route to incompletely-condensed silsesquioxanes: base-mediated cleavage of polyhedral oligosilsesquioxanes," Chem. Commun. (1999) 2309-2310.
P.D. Lickiss and F. Rataboul, "Chapter 1: Fully condensed polyhedral oligosilsesquioxanes (POSS): From synthesis to application," Adv. Organomet. Chem. vol. 57 (2008) 1-116.
F. J. Feher, "Controlled cleavage of R8Si8O12 frameworks: a revolutionary new method for manufacturing precursors to hybrid inorganic-organic materials," Chem. Commun. (1998) 399-400.
A. Tuteja et al., "Designing superoleophobic surfaces," Science. vol. 318 (2007) 1618-1622.
S. H. Phillips et al., "Developments in nanoscience: polyhedral oligomeric silsesquioxane (POSS)-polymers," Current Opinion in Solid State and Materials Science. vol. 8 (2004) 21-29.
W. Choi et al., "Fabrics with tunable oleophobicity," Adv. Mater. vol. 21 (2009) 2190-2195.
S. T. Iacono et al., "Facile synthesis of hydrophobic fluoroalkyl functionalized silsesquioxane nanostructures," Chem. Commun. (2007) 4992-4994.
J. M. Mabry et al., "Fluorinated polyhedral oliomeric silsesquioxanes (F-POSS)," Angew. Chem., Int. Ed. vol. 47 (2008) 4137-4140.
S. S. Chhatre et al., "Fluoroalkylated silicon-containing surfaces—estimation of solid-surface energy," Appl. Mater. Interfaces. vol. 2 (2010) 3544-3554.
E. G. Shockey et al., "Functionalized polyhedral oligosilsesquioxane (POSS) macromers: new graftable POSS hydride, POSS α-olefin, POSS epoxy, and POSS chlorosilane macromers and POSS-siloxane triblocks," Appl. Organomet. Chem. vol. 13 (1999) 311-327.
R. Duchateau, "Incompletely condensed silsesquioxanes: versatile tools in developing silica-supported olefin polymerization catalysts," Chem. Rev. vol. 102 (2002) 3525-3542.
C. Ohde et al., "Oxovandaium (IV) silsesquioxane complexes," Inorg. Chem. vol. 49 (2010) 2479-2485.
K. Pielichowski et al., "Polyhedral oligomeric silsesquioxane (POSS)-containing nanohybrid polymers," J. Adv. Polym. Sci. vol. 201 (2006) 225-296.
F. J. Feher et al., "Practical methods for synthesizing four incompletely condense silsesquioxanes from a single R8Si8O12 framework," Chem. Commun. (1998) 1279-1280.
D. B. Cordes et al., "Recent developments in the chemistry of cubic polyhedral oligosilsesquioxanes," Chem. Rev. vol. 110 (2010) 2081-2173.
A. Tuteja et al., "Robust omniphobic surfaces," PNAS. vol. 105 (2008) 18200-18205.
R. H. Baney et al., "Silsesquioxanes," Chem. Rev. vol. 95 (1995) 1409-1431.
F. J. Feher et al., "Synthesis and structural characterization of a remarkably stable, anionic, incompletely condensed silsesquioxane framework," Chem. Commun. (1997) 829-830.
H. Liu et al., "A spectroscopic investigation of incompletely condensed polyhedral oligomeric silsesquioxanes (POSS-mono-ol, POSS-diol and POSS-triol): hydrogen-bonded interaction and host-guest complex," J. Organomet. Chem. vol. 693 (2008) 1301-1308.
T. W. Dijkstra et al., "Silsesquioxane models for geminal silica surface silanol sites. A spectroscopic investigation of different types of silanols," J. Am. Chem. Soc. vol. 124 (2002) 9856-9864.
S. T. Iacono et al., "Preparation of composite fluoropolymers with enhanced dewetting using fluorinated silsesquioxanes as drop-in modifiers," J. Mater. Chem. vol. 20 (2010) 2979-2984.
F. J. Feher et al., "Facile framework cleavage reactions of a completely condensed silsesquioxane framework," J. Am. Chem. Soc. vol. 119 (1997) 11323-11324.
F. J. Feher et al., "Reactions of incompletely-condensed silsequioxanes with pentamethylantimony: a new synthesis of metal-lasilsesquioxanes with important implications for the chemistry of silica surfaces," J. Am. Chem. Soc. vol. 114 (1992) 3859-3866.
F. J. J Feher and T. L. Tajima, "Synthesis of a molybdenum-containing silsesquioxane which rapidly catalyzes the metathesis of olefins," J. Am. Chem. Soc. vol. 116 (1994) 2145-2146.
F. J. Feher et al., "Silsesquioxanes as models for silica surfaces," J. Am. Chem. Soc. vol. 111 (1989) 1741-1748.
H. M. Cho et al., "A Mo(VI) alkylidyne complex with polyhedral oligomeric silsesquioxane ligands: homogeneous analogue of a silica-supported alkyne metathesis catalyst," J. Am. Chem. Soc. vol. 128 (2006) 14742-14743.
J. D. Lichtenhan et al., "Linear hybrid polymer building blocks: methacrylate-functionalized polyhedral oligomeric silsesquioxane monomers and polymers," Macromol. vol. 28 (1995) 8435-8437.
T. S. Haddad and J. D. Lichtenhan, "Hybrid organic-inorganic thermoplastics: styryl-based polyhedral oligomeric silsesquioxane polymers," Macromol. vol. 29 (1996) 7302-7304.
K. Koh et al., "Precision synthesis of a fluorinated polyhedral oligomeric silsesquioxane-terminated polymer and surface charac-

(56) References Cited

OTHER PUBLICATIONS terization of its blend film with poly(methyl methacrylate)," Macromol. vol. 38 (2005) 1264-1270.

E. Lucenti et al., "Synthesis and characterization of osmium-containing silsesquioxanes: high-yield routes to {Os3 (CO)10(µ-H)[µ-O)Si7O10(c-C6H11)7]}and the new clusters {Os3(CO)10(µ-H)[µ-O)Si7O9(OH)2(c-C6H11)7]}, {[Os3 (CO)10(µ-H)]2[µ-O)2Si7O9(OH)(c-C6H11)7], {Os3(CO)10(µ-H)[µ-O)Si8O11(OH)(c-C6H11)8]}, and {[Os3(CO)10(µ-H)] 2(µ-O)2Si8O11(c-C6H11)8}," Organomet. vol. 26 (2006) 75-82.

K. Wada et al., "Synthesis and catalytic activity of group 4 metallocene containing silsesquioxanes bearing functionalized silyl groups," Organomet. vol. 23 (2004) 5824-5832.

K. Ohno et al., "Living radical polymerization by polyhedral oligomeric silsesquioxane-holding initiators; precision synthesis of tadpole-shaped organic/inorganic hybrid polymers," Macromol. vol. 37 (2004) 8517-8522.

S. T. Iacono et al, "Synthesis, characterization, and surface morphology of pendant polyhedral oligomeric silsesquioxane perfluorocyclobutyl aryl ether copolymers," Macromol. vol. 40 (2007) 9517-9522.

T. Haddad et al, "Polyhedral Oligomeric Silsequioxane (POSS)-Styrene Macromers" Organomet. vol. 11 (2001) 155-164.

R. Duchateau et al, "Silica-Grafted Diethylzinc and a Silsesquioxane-Based Zinc Alkyl Complex as Catalysts for the Alternating Oxirane-Carbon Dioxide Copolymerization" Organomet. vol. 26 (2007) 4204-4211.

Fina et al., "Polyhedral oligomeric silsesquioxanes (POSS) thermal degradation," Thermochimica Acta., vol. 440 (2006) 36-42.

Fina et al., "POSS-based hybrids by melt/reactive blending," J. Mater. Chem., vol. 20 (2010) 9297-9305.

Iyer et al., "Thermal and mechanical properties of blended polyimide and amine-functionalized poly(orthosiloxane) composites," J. Appl. Polym. Sci., vol. 108 (2008) 2691-2699.

Moore et al., "Asymmetric aryl polyhedral oligomeric silsesquioxanes (ArPOSS) with enhanced solubility," J. Organomet. Chem., vol. 696 (2011) 2676-2680.

Rosenberg et al., "Preparation of some arylchlorosilanes with arylmagnesium chlorides," J. Organomet. Chem., vol. 22 (1957) 1606-1607.

Wright et al., "Chemical modification of fluorinated polyimides: new thermally curing hybrid polymers with POSS," Macromol., vol. 39 (2006) 4710-4718.

Badrinarayanan et al., "Zirconium tungstate/cyanate ester nanocomposites with tailored thermal expansivity," Composites Sci Technol., vol. 71 (2011) 1385-1391.

Hamerton, "Studies on a dicyanate containing four phenylene rings and polycyanurate blends. 2. application of mathematical models to be catalysed polymerization process," Polymer, vol. 44 (2003) 4839-4852.

Hubbard et al., "Curing of a bisphenol E based cyanate ester using magnetic nanoparticles as an internal heat source through induction heating," Appl. Mater. Interf., vol. 5 (2013) 11329-11335.

Hudson and Nelson, University Physics 2d ed. 754 (Saunders College Publishing: Philadelphia 1990), p. 754.

Zhao et al., "Autocatalytic curing kinetics of thermosetting polymers: a new model based on temeprature dependent reaction orders," Polymer, vol. 51 (2010) 3814-3820.

Davis et al., "Polycyanurate networks from anethole ddimers: synthesis and characterization," J. Polym. Sci. Polym. Chem., vol. 50 (2012) 4127-4136.

Machine Translation, Chinese Patent Publication No. 102659827A (2012), 9 pages total.

United States Patent and Trademark Office, Non-Final Office Action in U.S. Appl. No. 13/624,355, mailed Sep. 24, 2014, 7 pages total.

United States Patent and Trademark Office, Non-Final Office Action in U.S. Appl. No. 13/748,730, mailed Jul. 22, 2014, 8 pages total.

United States Patent and Trademark Office, Non-Final Office Action in U.S. Appl. No. 14/013,600, mailed Aug. 22, 2014, 6 pages total.

United States Patent and Trademark Office, Final Office Action in U.S. Appl. No. 14/013,600, mailed Dec. 4, 2014, 5 pages total.

Braunecker et al., "Controlled/living radical polymerizations: features, developments, and perspectives," Prog. Polym. Sci., vol. 52 (2007) 98-146.

Cheng et al., "Phosphonium-containing ABA triblock copolymers: controlled free radical polymerization of phosphonium ionic liquids," Macromol., vol. 44 (2011) 6609-6617.

Crivello et al., "The synthesis, characterization, and photoinitiated cationic polymerization of silicon-containing epoxy resins," J. Polym. Sci. Part A: Polym. Chem., vol. 28 (1990) 479-503.

Destarac, "On the critical role of RAFT agent design in reversible addition-fragmentation chain transfer (RAFT) polymerization," Polym. Rev., vol. 51 (2011) 163-187.

Georjon et al., "Effects of crosslink density on mechanical properties of high glass transition temperature polycyanurate networks," J. Appl. Polym. Sci., vol. 65 (1998) 2471-2479.

Girard et al., "Direct synthesis of vinylidene fluoride-based amphiphilic diblock copolymers by RAFT/MADIX polymerization," ACS Macro Lett., vol. 1 (2012) 270-274.

Goto et al., "Mechanism and kinetics of RAFT-based living radical polymerizations of styrene and methyl methacrylate," Macromol., vol. 34 (2001) 402-408.

Gregory et al., "Complex polymer architectures via RAFT polymerization: from fundamental process to extending the scope using clink chemistry and nature's building blocks," Prog. Polym. Sci., vol. 37 (2012) 38-105.

Guenthner et al., "A new silicon-containing bis(cyanate) ester resin with improved thermal oxidation and moisture resistance," Macromol., vol. 39 (2006) 6046-6053.

Guenthner et al., "Cure characterization of tricyanate ester high-temperature composite resins," SAMPE Presentation (2011) 22 pages total.

Guenthner et al., "Synthesis, cure, kinetics, and physical properties of a new tricyanate ester with enhanced molecular flexibility," Polymer, vol. 52 (2011) 3933-3942.

Guenthner et al., "New insights into structure-property relationships in thermosetting polymers from studies of cocured polycyanurate networks," Macromol., vol. 45 (2012) 211-220.

Guenthner et al., "Effects of silicon substitution in the main chain network segments of polycyanurates," American Chemical Society National Conference, San Diego, CA (2012) 4 pages total.

Hay et al., "6: Processing and cure schedules for cyanate ester resins," Chem & Tech Cyanate Ester Resins (1994) 22 pages total.

Iacono et al., "Synthesis, characterization, and properties of chain terminated polyhedral oligomeric silsesquioxanefunctionalized perfluorcyclobutyl aryl ether copolymers," Polymer, vol. 28 (2007) 4637-4645.

Isemura et al., "Dichloropentafluoropropane as solvents for size exclusion chromatography," J. Chromatog. A., vol. 1026 (2004) 109-116.

Kumpfer et al., "Directed self-assembly of metallosupramolecular polymers at the polymer-polymer interface," ACS Macro Lett., vol. 1 (2012) 882-887.

Lu et al., "L-proline functionalized polymers prepared by RAFT polymerization and their assemblies as supported organocatalysts," Macromol., vol. 44 (2011) 7233-7241.

Marella, "An investigation on the hydrolysis of polyphenolic cyanate esters using near-IR spectroscopy," A Masters Thesis submitted to the faculty of Drexel University (2008) 102 pages total.

Maya et al., "Oligodimethylsiloxane linked cyanate ester resins," Macromol., vol. 35 (2002) 460-466.

Mayadunne et al., "Living radical polymerization with reversible addition-fragmentation chain transfer (RAFT polymerization) using dithiocarbamates as chain transfer agents," Macromol., vol. 32 (1999) 6977-6080.

McConnell, "Resins for the hot zone, part 1: polyimides," Composites World, available at http://www.compositesworld.com/articles/resins-for-the-hot-zone-part-i-polyimides (2009), accessed Dec. 17, 2012, 6 pages total.

McConnell, "Resins for the hot zone, part 2: BMIs, CEs, benzoxazines and phthalonitriles," Composites World, available at

(56) References Cited

OTHER PUBLICATIONS http://www.compositesworld.com/articles/resins-for-the-hot-zone-part-ii-bmis-ces-benzo . . . (2009), accessed Dec. 17, 2012, 6 pages total.
McCormick et al., "Aqueous RAFT polymerization: recent developments in synthesis of functional water-soluble (co) polymers with controlled structures," Acc. Chem. Res., vol. 37 (2004) 312-325.
Moad et al., "Toward living radical polymerization," Accounts of Chem. Res., vol. 41 (2006) 1133-1142.
Moad et al., "Some recent developments in RAFT polymerization," ACS Symp. Ser., vol. 1100 (2012) 243-258.
Moore et al., "Asymmetric aryl polyhedral oligomeric silisesquioxanes (ArPOSS) with enhanced solubility," J. Organomet. Chem., vol. 696 (2011) 2676-2680.
Moore et al., "Increasing the solubility of inert peripherally aromatic poss," ACS Division of Polymer Chem Document No. 154:410824, citing Polym. Preprints, vol. 52 (2011).
Ramirez et al., "Functionalization of fluoroalkyl polyhedral oligomeric silsesquioxanes (F-POSS)," ACS Symp. Ser., vol. 1106 (2012) 95-109.
Ramirez et al., "Incompletely condensed fluorozlkyl silsesquioxanes and derivatives: precursors for low surface energy materials,"JACS, vol. 133 (2011) 20084-20087.
Reams et al., "Effect of chemical structure and network formation of physical properties of di(cyanate ester) thermosets," Appl. Mater. Interfac., vol. 4 (2012) 527-535.
Roghani-Mamaquani et al., "In situ controlled radical polymerization: a review on synthesis of well-defined nanocomposites," Polym. Rev., vol. 52 (20120 142-188.
Shimp et al., "Cyanate esters—a new family of high temperature thermosetting resins," High Temp. Polym. (1989) 127-140.
Shimp et al., "Moisture effects and their control in the curing of polycyanate resins," ACS PMSE Prepr., vol. 66 (1992) 504-505.
Stamenovic et al., "Norbornenyl-based RAFT agents for the preparation of functional polymers via thiol-ene chemistry," Macromol., vol. 44 (2011) 5619-5630.
Tan et al., "Tailoring micelle formation and gelation in (PEG-P(MA-POSS)) amphiphilic hybrid block copolymers," Macromol., vol. 44 (2011) 622-631.
Thomas et al., "Kinetics and molecular weight control of the polymerization of acrylamide via RAFT," Macromol., vol. 37 (2004) 8941-8950.
Tsujii et al., "Mechanism and kinetics of RAFT-mediated graft polymerization of styrene on a solid surface. 1. experimental evidence of surface radical migration," Macromol,. vol. 34 (2001) 8872-8878.
Wang et al., "Hepta(3,3,3-trifluoropropyl) polyhedral oligomeric silsesquioxane-capped poly(N-isopropylacrylamide) telechelics: synthesis and behavior of physical hydrogels," Appl. Mater. & Interf., vol. 3 (2011) 898-909.
Wright, "The synthesis of new silane based bis(cyanate) ester monomers for use in high performance composite resins," Proc. American Chemical Society (2004) 2 pages total.
Yameen et al., "Polycyanurate thermoset networks with high thermal, mechanical, and hydrolytic stability based on liquid multifunctional cyanate ester monomers with bisphenol A and AF units," Macromol. Chem. Phys., vol. 209 (2008) 1673-1685.
Zeng et al., "Rapid deswelling and reswelling response of poly(N-isopropylacrylamide) hydrogels via formation of interpenetrating polymer networks with polyhedral olgiomeric silsesquioxane-capped poly(ehtylene oxide) amphiphilic telechelics," J. Phys. Chem. B., vol. 113 (2009) 11831-11840.
Zeng et al., "Organic-inorganic hybrid hydrogels involving poly(N-isopropylacrylamide) and polyhedral oligomeric silsesquioxane: preparation and rapid thermoresponsive properties," J. Polym. Sci. Part B Polym. Phys., vol. 47 (2009) 504-516.
Zeng et al., "Nanostructures and surface hydrophobicity of epoxy thermosets containing hepta(3,3,3-trifluorpropyl) polyhedral oligomeric silsesquioxane-capped poly(hydroxyether of bisphenol A) telechelics," J. Colloid Interf. Sci., vol. 363 (2011) 250-260.
Zhang et al., "Synthesis via RAFT polymerization of tadpole-shaped organic/inorganic hybrid poly(acrylic acid) containing polyhedral oligomeric silsesquioxane (POSS) and their self-assembly in water," Macromol., vol. 42 (2009) 2563-2569.
Brenier, "Bifunctional surfaces with superhydrophobic and plasmonic properties," J. Phys. Chem. C., vol. 115 (2011) 10544-10549.
Campos et al., "Fluoroalkyl-functionalized silica particles: synthesis, characterization, and wetting characteristics," Langmuir, vol. 27 (2011) 10206-10215.
Campos et al., "Superoleophobic surfaces through control of sprayed-on stochastic topography," Langmuir, vol. 28 (2012) 9834-9841.
Ogawa et al., "Development of a transparent and ultrahydrophobic glass plate," Jpn. J. Appl. Phys., vol. 32 (1993) L614-L615.
Sagiv et al., "Organized monolayers by adsorption. 1. formation and structure of oleophobic mixed monolayers on solid surfaces," JACS, vol. 102 (1980) 92-98.
United States Patent Office, "Non-Final Office Action in U.S. Appl. No. 13/210,915," mailed Jun. 11, 2014, 6 pages total.
B. Seurer et al.., "Influences of POSS peripheral, architecture, and spacer group on phenylethynphthalimide reactions," Polymer Preprints, vol. 50 (2009) 820-821.
United States Patent and Trademark Office, Final Office Action in U.S. Appl. No. 13/159,950, mailed Apr. 9, 2015, 13 pages total.
United States Patent and Trademark Office, Non-Final Office Action in U.S. Appl. No. 14/013,600, mailed May 27, 2015, 10 pages total.

* cited by examiner

US 9,249,313 B2

SYNTHESIS OF FUNCTIONAL FLUORINATED POLYHEDRAL OLIGOMERIC SILSESQUIOXANE (F-POSS)

Pursuant to 37 C.F.R. §1.78(a)(4), this application claims the benefit of and priority to prior filed Provisional Application Ser. No. 61/537,122, filed Sep. 21, 2011. This application is related to Provisional Application Ser. No. 61/537,125, filed Sep. 21, 2011, and U.S. application Ser. No. 13/624,355, entitled SYNTHESIS AND APPLICATIONS OF PERIPHERALLY ASYMMETRIC ARYL POSS COMPOUNDS, filed Sep. 21, 2012. The disclosures of these applications are expressly incorporated herein by reference, in their entireties.

RIGHTS OF THE GOVERNMENT

The invention described herein may be manufactured and used by or for the Government of the United States for all governmental purposes without the payment of any royalty.

FIELD OF THE INVENTION

The present invention relates generally to silsesquioxane materials and, more particularly to silsesquioxane materials having increased hydrophobicity.

BACKGROUND OF THE INVENTION

Polyhedral Oligomeric SilSesquioxanes ("POSS") are cage-structures having a silicon-oxide ($SiO_{1.5}$) core surrounded by aliphatic or aromatic organic functionality. One such POSS derivative, octakis(1H,1H,2H,2H-heptadecafluorodecyl) POSS ("F-POSS"), possesses a periphery of long-chain fluorinated alkyl groups and has been determined to possess the lowest surface energy value of any crystalline solid ($\gamma_{sv}$=9.3 mN/m). Superhydrophobic (contact angles of a water droplet exceeding 150°) and oleophobic (repelled by oil) surfaces have been produced by casting F-POSS materials onto a substrate or blending the F-POSS material into a polymer matrix.

Conventionally, F-POSS has been used as standalone compounds without further reactive chemical functionality; however, this absence of reactive chemical functionality limits solubility in common solvents, the mechanical robustness, and abrasion resistance of surfaces comprising these materials. One attempt to overcome such limitations has been an incompletely-condensed F-POSS compound with silanol functionality, which enabled new, robust, low surface energy hybrid materials. In fact, incompletely-condensed silsesquioxane frameworks have emerged with alkyl and/or aryl peripheries and are operable as synthons for creating hybrid inorganic-organic materials, as models for silica, for catalyst support, and as precursors for other silsesquioxane containing polymers.

Unfortunately, none of the conventional synthesis strategies are viable to produce long-chain (more than three carbon atoms) F-POSS compounds possessing additional reactive or non-reactive functionality beyond alkyl or aryl peripheries. Exemplary strategies, such as those described in U.S. Pat. No. 7,053,167, entitled SILSESQUIOXANE DERIVATIVE HAVING FUNCTIONAL GROUP, issued to Ito et al. on Apr. 8, 2004 and U.S. Pat. No. 7,291,747, entitled NOVEL SILICON COMPOUNDS AND PROCESS FOR PREPARATION THEREOF, issued to Oikawa et al. on Nov. 6, 2007 (disclosures incorporated herein by reference, in their entireties), have not produced long-chain F-POSS-$(ONa)_3$ having more than three carbon atoms. Modified methods have produced $(3,3,3\text{-trifluoropropyl})_7Si_7O_9(ONa)_3$, which can be derivatized with long-chain fluorinated trichlorosilanes to produce low surface energy materials, but the trifluoropropyl groups are still limited in chain length.

While these conventional methods have proven successful for the synthesis of incompletely-condensed compounds possessing alkyl- and aryl-functionality, there remains a need for a method of synthesizing an incompletely-condensed, long-chain F-POSS compound.

SUMMARY OF THE INVENTION

The present invention overcomes the foregoing problems and other shortcomings, drawbacks, and challenges of synthesizing an incompletely-condensed, long-chain F-POSS compound. While the invention will be described in connection with certain embodiments, it will be understood that the invention is not limited to these embodiments. To the contrary, this invention includes all alternatives, modifications, and equivalents as may be included within the spirit and scope of the present invention.

According to one embodiment of the present invention a functional fluorinated polyhedral oligomeric silsesquioxane ("F-POSS") has a chemical structure:

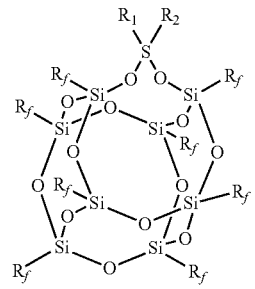

where $R_f$ represents a nonreactive organic group and at least one of $R_1$ and $R_2$ represents a chain comprising at least three carbon atoms.

According to another embodiment of the present invention, a method of manufacturing the F-POSS includes opening a single edge of a closed-cage F-POSS and bridging the opened, single edge with a sulfate group. The sulfate group is converted to a disilanol and then reacted with a functional dichlorosilane. The dichlorosilane includes at least one organic functional group comprising at least three carbon atoms.

Still other embodiments of the present invention include a method of forming a hydrophobic and oleophobic surface by spin coating an inert surface with the F-POSS.

One embodiment of the present invention is directed to a hydrophobic and oleophobic that includes an inert substrate and a film coating the substrate. The film includes monomers of F-POSS and a co-polymer.

The above and other objects and advantages of the present invention shall be made apparent from the accompanying drawings and the descriptions thereof.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

DETAILED DESCRIPTION OF THE INVENTION

Figure 1:
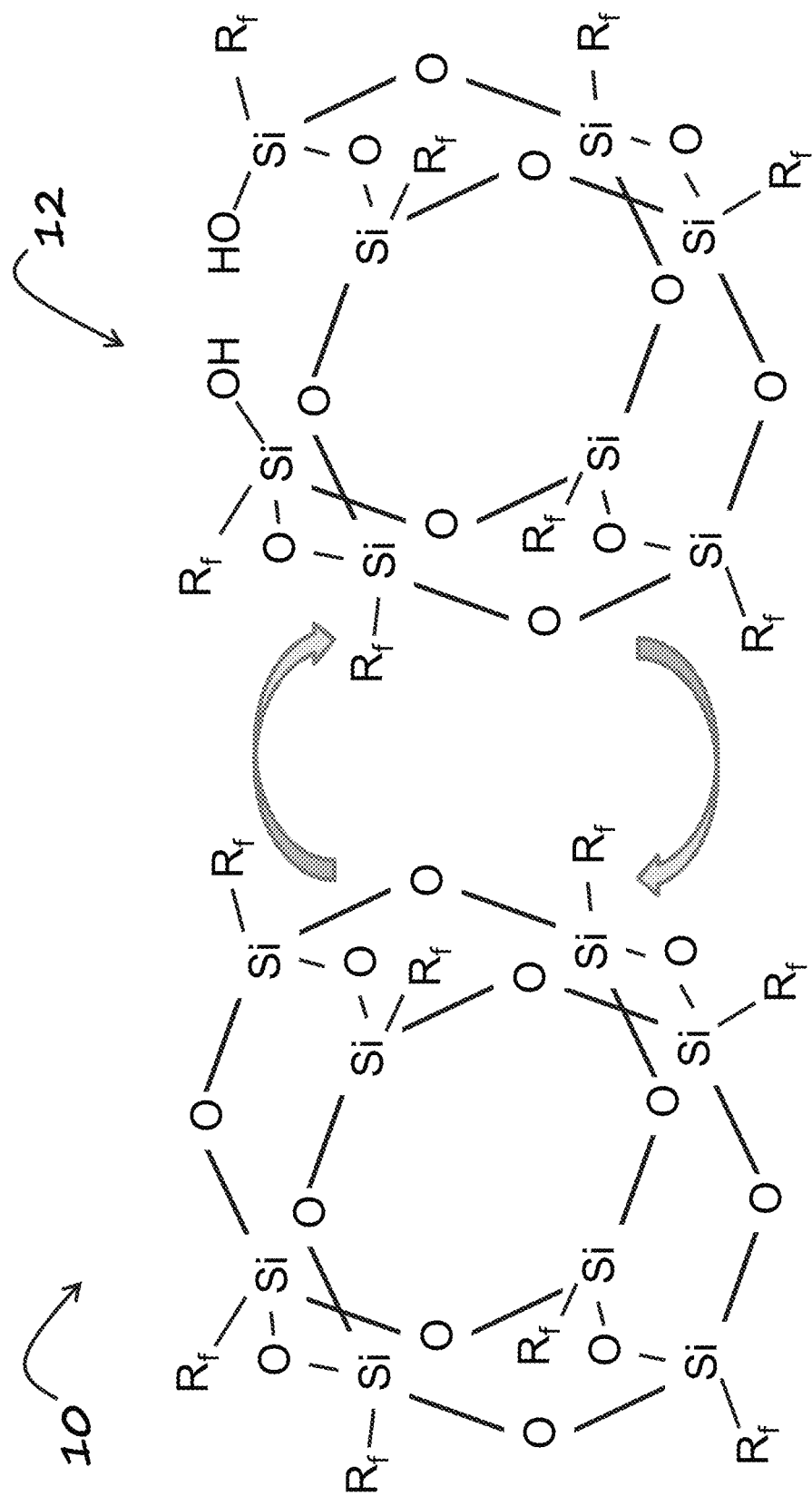
FIG. 1 is a schematic representation of the synthesis of one embodiment of an incompletely-condensed fluoroalkyl silsesquioxane.
Figure 2:
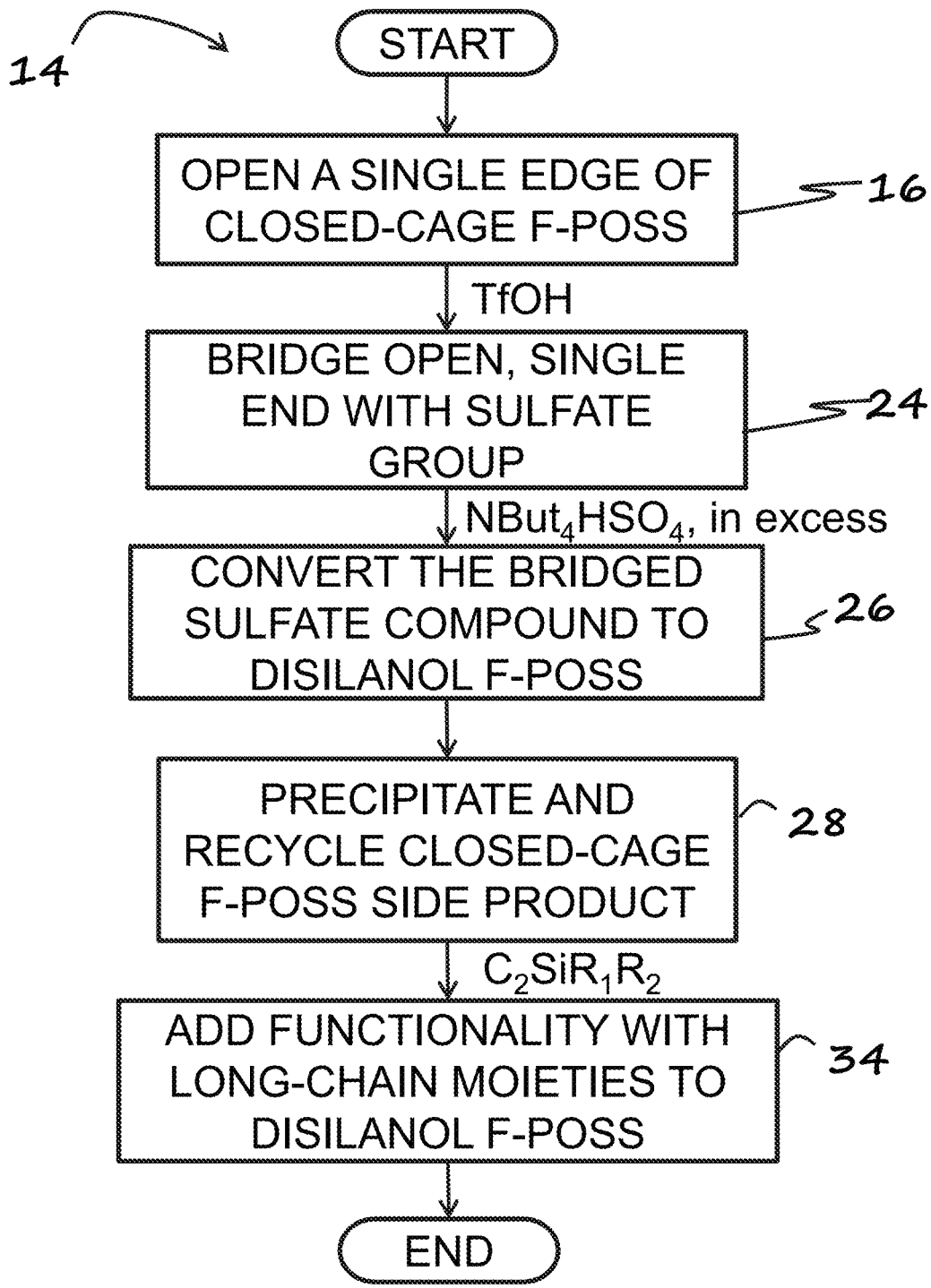
FIG. 2 is a flow chart illustrating a method of synthesizing an incompletely-condensed fluoroalkyl silsesquioxane in accordance with one embodiment of the present invention.

Turning now to the figures, and in particular to FIGS. 1 and 2, a multi-step synthetic method for converting a closed-cage F-POSS compound 10 to an incompletely-condensed silsesquioxane compound 12 (hereafter, "disilanol F-POSS" 12), $((R_f)_8Si_8O_{11}(OH)_2)$ is shown and described in detail. While not necessary, but for purposes of illustration, the F-POSS compound 10 includes nonfunctional groups, $R_f$, which may comprise —$CH_2CH_2(CF_2)_7(CF_3)$; however, other moieties, may also be included. Indeed, not all $R_f$ groups are required to have the same functionality.

Figure 3:
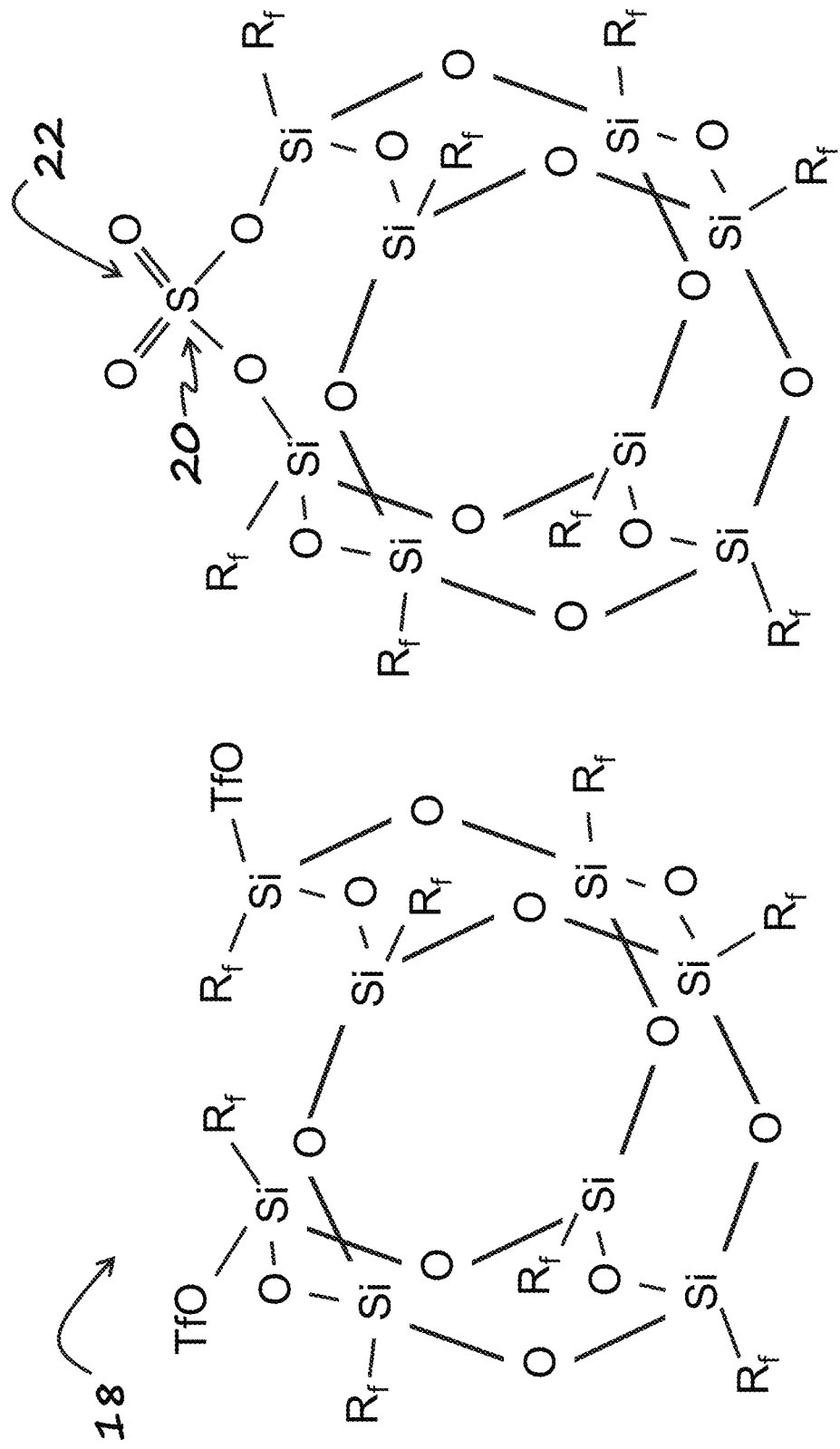
FIGS. 3A and 3B are schematic representations of two intermediates in the synthesis of FIG. 1.

More particularly, and as provided in the flow chart 14 of FIG. 2, a single edge of the closed-cage F-POSS compound is opened (Block 16) with trifluoromethane sulfonic acid, such as triflic acid ("TfOH"), in $C_6F_6$ and $CF_3SO_3H$ at 25° C. for 75 min. to form a first, unstable intermediate, which is illustrated herein as ditriflate POSS cage 18, $((R_f)_8Si_8O_{11}(OTf)_2)$, which is shown in FIG. 3A. Presence of the ditriflate POSS cage formation was confirmed, despite spectral complexity, via $^{29}Si$ NMR. The spectrum demonstrated an equilibrium between the open and closed-cage silsesquioxane frameworks 10, 18, with resonances at −62.6 ppm, −65.0 ppm, and −67.7 ppm and an integrated ratio of 2:2:4. While not wishing to be bound by theory, it is thought that the inability to isolate the first intermediate, ditriflate POSS 18, may be attributed to the strong electron-withdrawing effects of the fluorinated alkyl groups, $R_f$.

The open, single end of the ditriflate compound 18 may then be bridged with a sulfate group 20 to a second, unstable intermediate, a bridged sulfate compound 22 (FIG. 3B), $((R_f)_8Si_8O_{13}(SO_2))$, in Block 24 over a reaction time, for example, of approximately 30 min., with an excess of $NBut_4HSO_4$, under nitrogen. The reaction mixture separates into two liquid layers: a first, yellow aqueous layer and a second, colorless fluorinated solvent layer containing both of the closed-cage F-POSS compound 10 (FIG. 1) and the bridged sulfate compound 22. While the bridging sulfate moiety 20 appears to stabilize the electron-withdrawing F-POSS cage framework, the bridged sulfate compound 22 cannot be isolated. Its presence is confirmed, however, as another NMR-observed intermediate with $^{29}Si$ resonances at −64.5 ppm, −65.7 ppm, and −67.3 ppm with an integrated ratio of 2:2:4. Although the bridged sulfate compound 22 was not isolated, its endohedral geometry was deduced from x-ray crystallography data, described in detail below.

Referring again to FIG. 2, a polar fluorinated solvent/water mixture (for, example, a 10:1 ratio of solvent to water) is added to the fluorinated solvent layer (the colorless, aqueous layer above) of the reaction mixture for a time ranging from about 6 hours to about 12 hours to convert the bridged sulfate compound 22 to the disilanol F-POSS 12 of FIG. 1 (Block 26). Because the reaction requires water to be miscible with the fluorinated solvent, the polar fluorinated solvent/water mixture is necessary to yield the desired, disilanol compound.

To isolate the disilanol F-POSS 12, ethyl acetate is added to the reaction mixture, and subsequently filtered. The filtrate is collected, concentrated, suspended again in chloroform, and filtered. The collected filtrand is dried under vacuum (about 18 hours at 50° C.) to yield the product with an overall yield of approximately 53% and a molecular weight of 4009 g/mol.

The principle side product of the conversion (Block 26) is the closed cage F-POSS compound 10. Due to subtle differences in solubility between the closed cage F-POSS 10 and the disilanol F-POSS 12, disilanol F-POSS 12 may be purified from the closed cage F-POSS 10, the latter of which may be subsequently recycled (Block 28). In accordance with one embodiment of the present invention, the closed cage F-POSS 10 may be precipitated from the reacted polar fluorinated solvent/water mixture while the disilanol F-POSS 12 is subsequently precipitated from a $CHCl_3$ solution.

The structure of disilanol F-POSS 12 was determined by combustion analysis and multinuclear NMR ($^1H$, $^{13}C$, $^{19}F$, and $^{29}Si$). The $^{29}Si$ NMR spectrum displayed peaks at −59.0 ppm, −65.5 ppm, and −68.1 ppm, with an integration ratio of 2:2:4, which are attributed to the $C_{2v}$ symmetry of silsesquioxane. The peak at −59.0 ppm is attributed to the silanol groups of the POSS framework.

Figure 4:
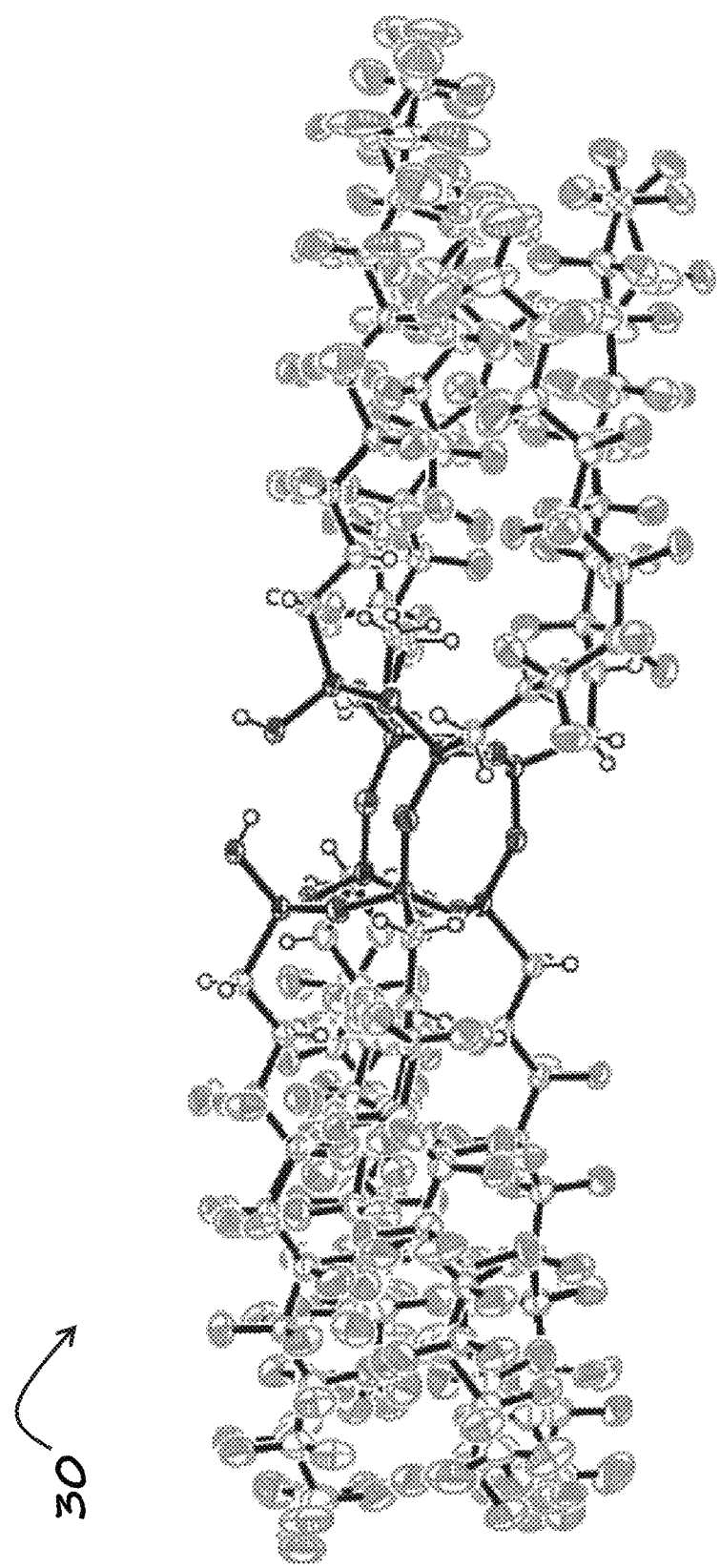
FIG. 4 is a schematic representation of a crystal structure determined for the incompletely-condensed fluoroalkyl silsesquioxane.

The crystal structure 30 for disilanol F-POSS 12, shown in FIG. 4, was obtained by growing crystals from slow evaporation in hexafluorobenzene and using a 3-circle SMART-APEX CCD (Kusing Bruker, Billerica, Mass.) with c-axis fixed at 54.748 and temperature of about 100 K with SMART V 5.625 program. Graphite monochromated $Cu_{K\alpha}$ ($\lambda=1.54179$ Å) radiation was used for data collection, the SAINT V 6.22 program (Bruker, Corp.) was used for correcting Lorentz and polarization effects, and the SADABS program (Bruker, Corp.) was used for reflection scaling.

The structure was solved from $C_6F_6$ by direct methods (SHELXL-97, Bruker, Corp.) and all non-hydrogen atoms refined anisotropically using full-matrix, least squares refinement on $F^2$ and determined to be monoclinic P2(1)/c. The structure contains rigid, helical-like fluoroalkyl chains that are similar to the closed cage F-POSS 10 (FIG. 1) but are attached to the open Si—O frame-work by methylene groups. The crystal structure supports the 2:2:4 ratio of silicon atoms as determined by $^{29}Si$ NMR spectroscopy of silicon atoms.

Figure 5:
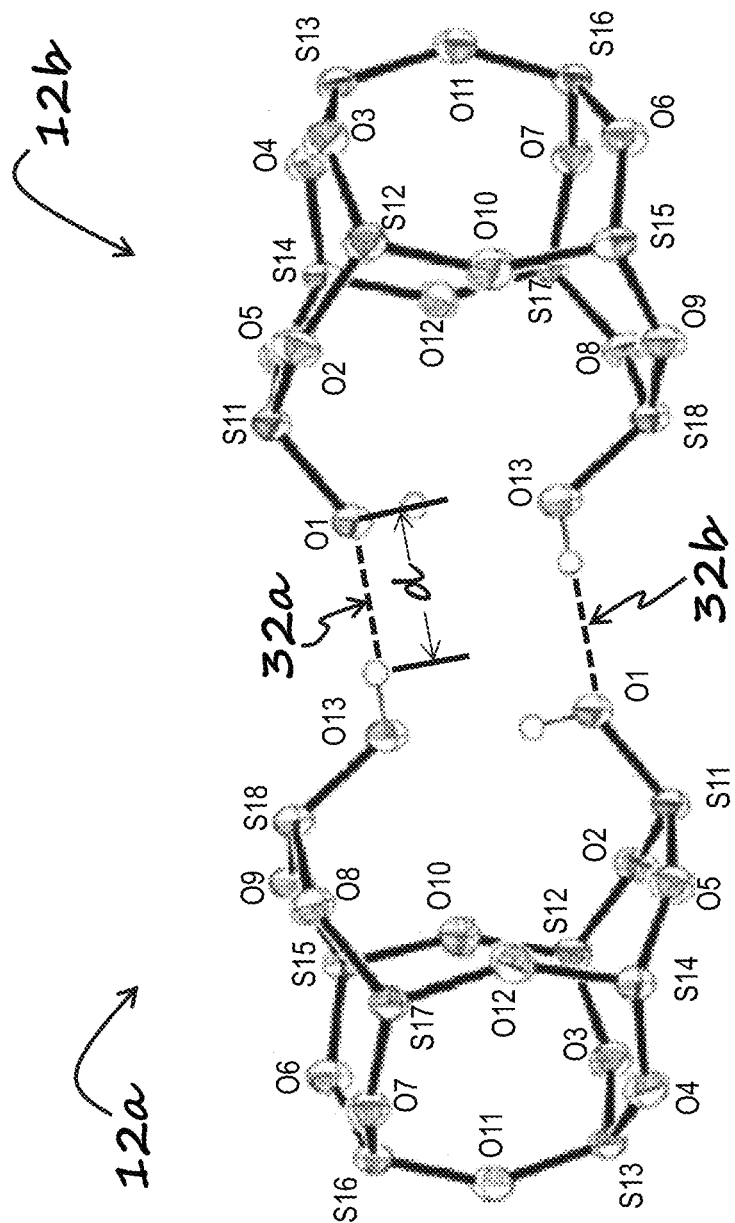
FIG. 5 is a schematic representation of a portion of the crystal structure of FIG. 4, showing the intermolecular hydrogen bonding.

The crystal packing of two disilanol F-POSS molecules (illustrated as 12a and 12b in FIG. 5, specifically, and in FIG. 6, generally, as crystal packing) reveals a dimeric structure with two F-POSS cages forming intermolecular hydrogen bonds 32a, 32b between silanol groups on of adjacent ones of the F-POSS cages 12a, 12b. This induces an increase in the lattice volume (approximately 12884 Å$^3$) for disilanol F-POSS 12 as compared to the volume of the closed cage F-POSS 10, which was approximately 6340 Å$^3$. Like the hydrogen bonding between silanols on incompletely-condensed alkyl based POSS triols and diols, a dimeric contact is established from intermolecular disilanol compounds at a distance, d, of approximately 2.798 Å. These intermolecular silanols are slightly closer than intramolecular silanols, (illustrated on FIG. 5 as O1, O2, O3, O4, O5, O6, O7, O8, O9, O10, O11, O12, and O13), which are separated by a distance of approximately 2.810 Å. As described in detail below, the intermolecular silanols are reactive to chlorosilanes.

To achieve an effective convergence on the structure, certain restrains were applied, including, for example, as the thermal behavior of the structure (SIMU and DELU commands for Si1 to F36C); ISOR was applied to fluorine atoms due to the associated disorder, intermolecular distances (C—C and C—F) were retrained using the SAME command. After a stable minimum was achieved, hydrogen atoms were added at calculated positions to the alpha and beta carbon atoms. Hydrogen atoms on O1 and O13 were added using DFIX to restrain the distances (0.84 Å) to the respective oxygen atoms.

Additional details with respect to the crystal structure may be obtained from the Cambridge Crystallographic Data Centre, available at http://www.ccdc.com.ac.uk, Deposition Number 843485, the disclosure of which is incorporated herein by reference, in its entirety.

Figure 6:
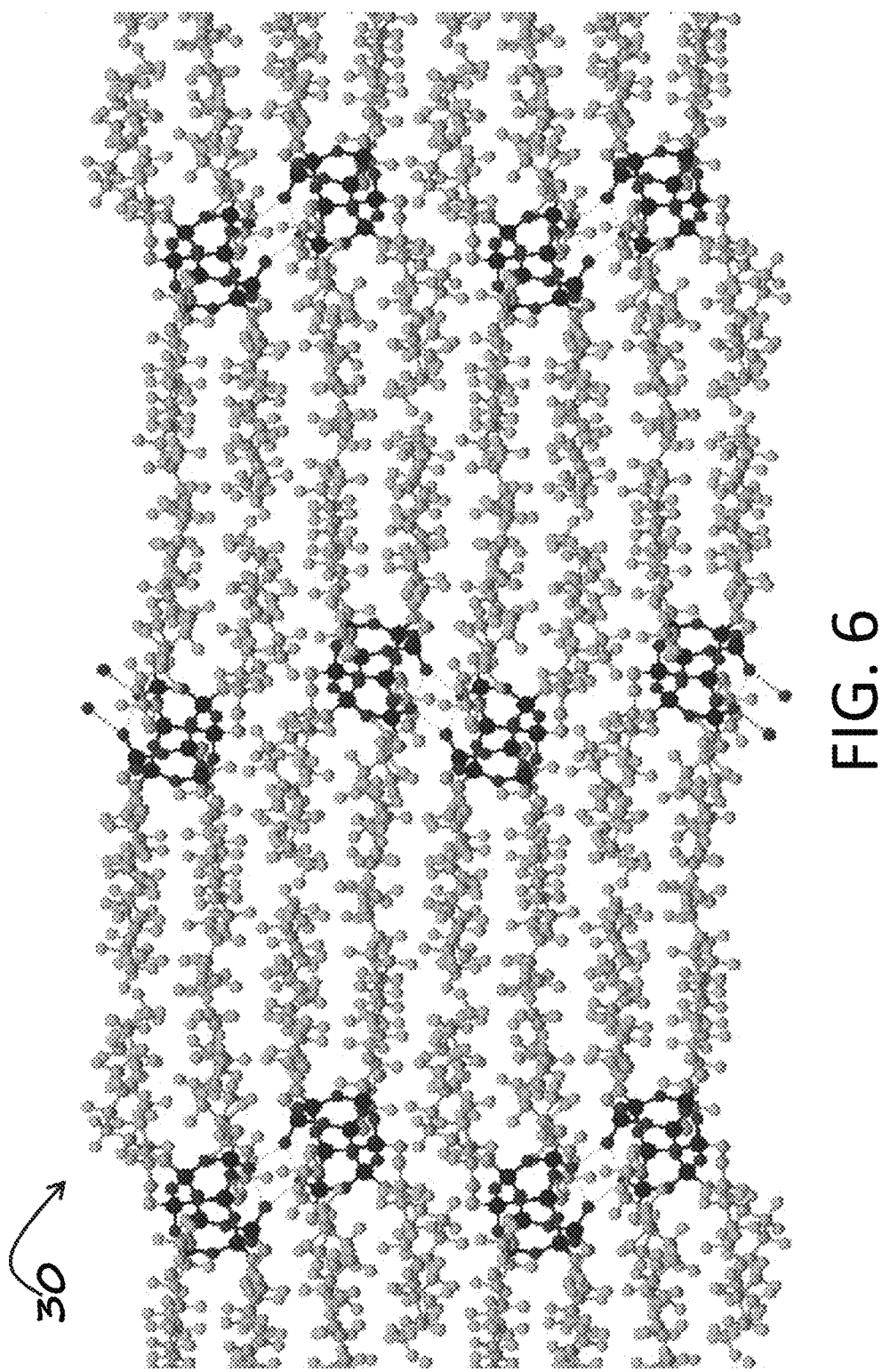
FIG. 6 is a schematic representation of crystal packing of a plurality of incompletely-condensed fluoroalkyl silsesquioxane, illustrating the hydrogen bonds between silanols.
Figure 7:
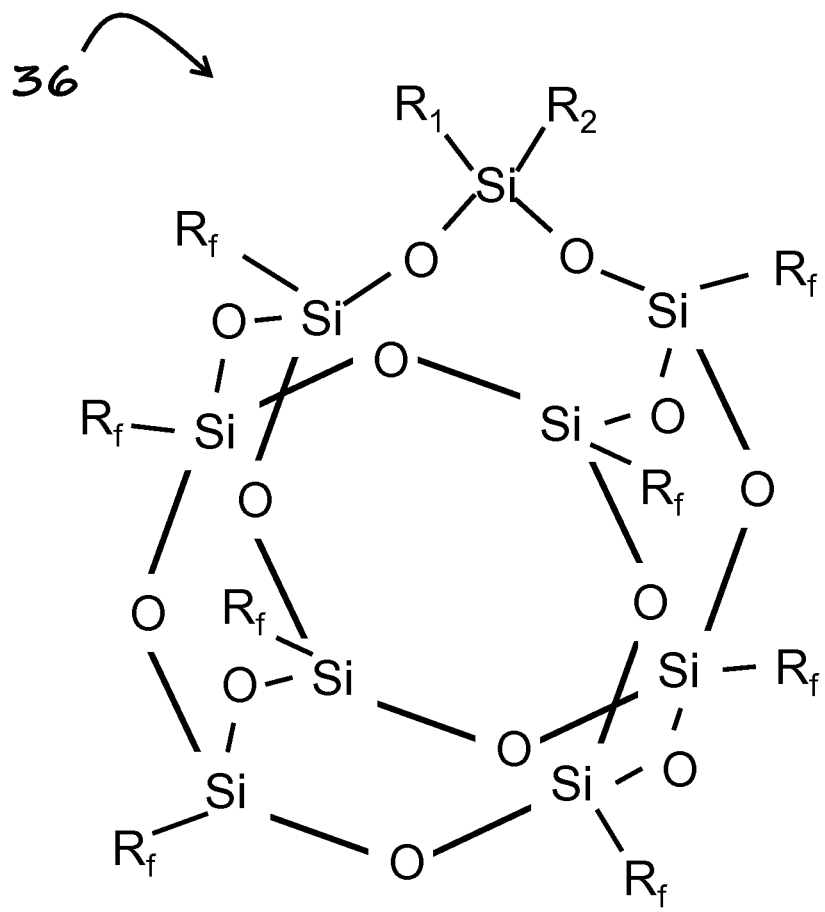
FIG. 7 is a schematic representation of the synthesis of one embodiment of a functionalized F-POSS compound.

Referring now to FIGS. 1, 2, and 6, disilanol F-POSS 12 is shown to readily react with functional dichlorosilanes ($Cl_2SiR_1R_2$) to add a particular or desired functionality (Block 34), which may include, for example, superhydrophobic or oleophobic properties. According to one embodiment of the present invention, the disilanol F-POSS 12 was condensed with bis(n-octyl)dichlorosilane in the presence of triethylamine to yield a functionalized F-POSS compound 36 (approximately 46% yield), shown in FIG. 7, with a loss of HCl. More particularly, bis(n-octyl)dichlorosilane and disilanol F-POSS 12, in $C_6F_6$, are mixed for 20 minutes and followed with the addition of triethylamine, in $C_6F_6$, and further mixing for about 12 hours. The solution is filtered and poured into ethyl acetate, causing white solid precipitate formation. Precipitate was removed via vacuum filtration, concentrated, dissolved in diethyl ether, and filtered again. The filtrate is then collected and cooled to 0° C., affording a white precipitate, which is collected and dried under vacuum to a white powder. The primary side product isolated during the reaction was, again, the closed cage F-POSS 10 (FIG. 1).

Evaluation of the structure of the functionalized F-POSS compound 36 included multinuclear NMR ($^1H$, $^{13}C$, $^{19}F$, and $^{29}Si$), FT-IR, and combustion analysis. NMR spectra were obtained on 300 MHz and 400 MHz spectrometers (Bruker Corp.) using 5 mm o.d. tubes. An inverse gated 30° pulse with a 12 second delay was used to acquire the $^{29}Si$ NMR spectra. The NMR spectrum produced $^{29}Si$ resonances at −17.8 ppm, −65.4 ppm, −68.2 ppm, and −69.0 ppm, with a ratio of 1:2:4:2, of which the resonance at −17.8 ppm was attributed to dioctyl-functionalized Si atom. Large C—H stretches observed at 2974 $cm^{-1}$ and 2871 $cm^{-1}$ in the FT-IR spectrum (Perkin Elmer Spectrum BX; Waltham, Mass.) supported the presence of the hydrocarbon chains, $R_1$, $R_2$.

As described herein, incompletely-condensed disilanol F-POSS compounds may be synthesized from fully condensed F-POSS compounds via a three-step reaction process and are reactive toward dichlorosilanes to produce a functional F-POSS compound. Crystal structures demonstrate silanol groups are hydrogen bonded via intermolecular interaction, which lowers the surface energy value beyond values observed with alkyl or aryl F-POSS compounds. Accordingly, the novel, tunable structure of the functionalized F-POSS compounds described herein provides unprecedented access to fluorinated building blocks for manufacturing low surface energy materials that are mechanically robust and abrasion resistant. For example, functionalized F-POSS 36 may be cast onto a substrate or blended with copolymers to produce surfaces having robust, abrasion resistant, superhydrophobic, and oleophobic material properties.

The following examples and comparative example illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

Example 1

Seven, long-chain F-POSS compounds, each having a different functional group, were prepared in accordance with embodiments of the present invention. The F-POSS compounds included F-POSS (no additional functional group), dihydroxy silyl F-POSS (Si—$(OH)_2$), dioctyl silyl F-POSS (Si—$((CH_2)_7CH3)_2$), dihexyl silyl F-POSS (Si—$(C_6H_5)_2$), vinyl methylsilyl F-POSS (Si—$(CH_3)(CH=CH_2)$), acrylate methylsilyl F-POSS (Si—$((CH_3((CH_2)_3OC(O)CCH=CH_2))$, and methylacrylate methylsilyl F-POSS (Si—$(CH_3)((CH_2)_3OC(O)C(CH_3)=CH_2))$. The synthesis of each compound was confirmed using combustion analysis, FT-IR, and multinuclear NMR spectroscopy.

The long-chain fluoroalkyl periphery on F-POSS results in desirable low surface energy characteristics. Interestingly, once a non-fluorinated segment was added to an edge of F-POSS, the solubility properties change dramatically. For example, the long hydrocarbon chains present in dioctyl silyl F-POSS expanded solubility from just fluorinated solvents to include non-fluorinated solvents, such as $Et_2O$ and $CHCl_3$. Even small organic modifications, such as the acrylate and methacrylate moieties on acrylate methylsilyl F-POSS and methylacrylate methylsilyl F-POSS, respectively, were sufficient to expand solubility to nonfluorinated solvents, such as $Et_2O$. However, phenyl and vinyl groups of dihexyl silyl F-POSS and vinyl methylsilyl F-POSS, respectively, did not improve the solubility in non-fluorinated solvents, which may be attributed to the rigidity of the phenyl and vinyl groups.

Films of each of the seven F-POSS compounds were spin cast onto seven wafers (1 inch silicon) from solutions of Asahiklin-255 (3,3-dichloro-1,1,1,2,2,-penta-fluoropropane/1,3-dichloro-1,1,2,2,3-pentafluoropropane) (10 mg/mL) at a rate of 900 rpm for 30 seconds and in accordance with the methods described in S. S. CHHATRE et al. "Fluoroalkylated Silicon-Containing Surfaces—Estimation of Solid-Surface Energy," *ACS Appl. Mater. Interfaces*. Vol. 2 (2010) 3544-3554, the disclosure of which is incorporated herein by reference, in its entirety. Dihydroxy silyl F-POSS was spin cast in a similar manner but from $C_6F_6$ solution at a rate of 1400 rpm. Surfaces were smoothed to less than 5 nm rms roughness to minimize any influence of surface roughness and topology as measured via atomic force microscopy using a Nanoscope IV (Digital Instruments, Inc., whole-owned subsidiary of Veeco Instruments, Inc., Plainview, N.Y.) and optical profilometry using a Wyko NT930 (Veeco Instruments, Inc.).

The influence of functionality on non-wetting behavior was determined by examining static and dynamic contact angles of water and hexadecane on each F-POSS film surface. Water and hexadecane 10 μL droplets were positioned on the prepared wafers. Dynamic contact angles were determined by placing a 3 μL drop of the probing liquid onto a test substrate of a DataPhysics OCA20 goniometer (DataPhysics Instruments GmbH, Filderstadt, Germany). An additional 2 μL of the probing liquid was added through a dispensing needle at a rate of 0.2 μL/sec and then 3 μL removed at 0.2 μL/sec. Video (ranging from 20 frames to 100 frames) was captured during the addition and removal of the probing liquid such that advancement and recession of a contact line between the droplet and the test substrate, respectively, was observed and used for determining the advancing and receding contact angles, respectively. Measurements were made from a "tangent lean" fit using a droplet fitting software (DataPhysics Instruments GmbH).

The open-cage framework of compound dihydroxy silyl F-POSS did not display any adverse effect on the wetting behavior, which was attributed to the dimeric structure formed with silanols shielded from the surface of the film. A slight increase in contact angle hysteresis, $\theta_{rec}-\theta_{adv}$, for dioctyl silyl F-POSS, vinyl methylsilyl F-POSS, acrylate methylsilyl F-POSS, and methylacrylate methylsilyl F-POSS was observed when wetted with water. This slight increase was not observed for surfaces comprising the same films when wetted with hexadecane, except for dioctyl silyl F-POSS. The structure of dioctyl silyl F-POSS contains long aliphatic chains that potentially favor interaction with a long-chain organic solvent, such as hexadecane.

Dihydroxy silyl F-POSS and dihexyl silyl F-POSS displayed the lowest hexadecane hysteresis values of all film surfaces and possessed sliding angles of approximately 7°. These initial measurements demonstrate that modifications of the F-POSS structure were found to be influential on wetting properties, either increasing or decreasing contact angle hysteresis.

TABLE 1

| LONG-CHAIN F-POSS | WATER | | HEXADECANE | |
|---|---|---|---|---|
| | ($\theta_{adv}$, degrees) | ($\theta_{rec}$, degrees) | ($\theta_{adv}$, degrees) | ($\theta_{rec}$, degrees) |
| F-POSS | 124.0 ± 0.5 | 109.6 ± 0.7 | 79.1 ± 0.4 | 65.1 ± 0.5 |
| Dihydroxy silyl F-POSS | 116.8 ± 0.4 | 111.0 ± 0.6 | 77.4 ± 0.4 | 74.4 ± 0.8 |
| Dioctyl silyl F-POSS | 117.9 ± 0.5 | 95.5 ± 0.4 | 69.1 ± 1.2 | 23.1 ± 1.2 |
| Dihexyl silyl F-POSS | 116.2 ± 0.4 | 110.5 ± 0.5 | 76.0 ± 0.8 | 73.2 ± 0.4 |
| Vinyl methylsilyl F-POSS | 116.2 ± 0.4 | 100.6 ± 0.8 | 78.4 ± 0.3 | 70.6 ± 2.3 |
| Acrylate methylsilyl F-POSS | 118.2 ± 1.0 | 90.6 ± 1.0 | 76.8 ± 0.3 | 67.8 ± 1.0 |
| Methylacrylate methylsilyl F-POSS | 117.0 ± 0.6 | 93.8 ± 1.5 | 78.1 ± 0.4 | 63.0 ± 1.2 |

While the present invention has been illustrated by a description of various embodiments, and while these embodiments have been described in some detail, they are not intended to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with methods of practicing the present invention as currently known. However, the invention itself should only be defined by the appended claims.

What is claimed is:

1. A functional fluorinated polyhedral oligomeric silsesquioxane ("F-POSS") comprising:
a chemical structure:

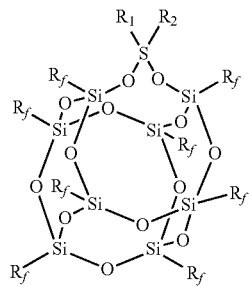

where each $R_f$ represents a nonreactive, fluorinated organic group; and
$R_1$ represents a first monovalent organic group comprising at least two carbon atoms and $R_2$ represents hydrogen or a second monovalent organic group comprising at least two carbon atoms.

2. The functional F-POSS of claim 1, wherein $R_f$ represents —CH$_2$CH$_2$(CF$_2$)$_7$CF$_3$.

3. The functional F-POSS of claim 1, wherein the $R_1$ is selected from a group consisting of —(CH$_2$)$_7$CH$_3$, —CH$_2$CH$_2$CH$_2$OC(O)CH═CH$_2$, and —CH$_2$CH$_2$CH$_2$OC(O)C(CH$_3$)═CH$_2$.

4. The functional F-POSS of claim 1, wherein the first monovalent organic group, the second monovalent group, or both comprises at least three carbon atoms.

5. The functional F-POSS of claim 1, wherein $R_f$ represents a fluorinated alkyl group.

6. The functional F-POSS of claim 1, wherein each $R_f$ is separately selected from the group consisting of fluorotetradecyl, fluorododecyl, fluorodecyl, fluorooctyl, fluorohexyl, and hexafluoro-i-butyl.

7. The functional F-POSS of claim 1, wherein each fluorinated alkyl group includes at least four carbons.

8. A functional fluorinated polyhedral oligomeric silsesquioxane ("F-POSS") comprising:
a chemical structure:

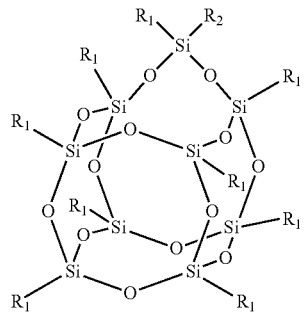

where each $R_f$ represents a fluorinated alkyl group; and
$R_1$ represents a first group having at least two carbon atoms and $R_2$ represents hydrogen or a second group having at least two carbon atoms.

9. The functional F-POSS of claim 8, wherein $R_1$ is selected from the group consisting of —(CH$_2$)$_7$CH$_3$, C$_6$H$_5$, CH═CH$_2$, —(CH$_2$)CH═CH$_2$, —(CH$_2$)$_3$OC(O)CH═CH$_2$, and —(CH$_2$)$_3$OC(O)C(CH$_3$)═CH$_2$.

10. The functional F-POSS of claim 9, wherein $R_2$ is selected from the group consisting of —CH$_3$, —(CH$_2$)$_7$CH$_3$, —C$_6$H$_5$, —CH═CH$_2$, (CH$_2$)CH═CH$_2$, —(CH$_2$)$_3$OC(O)CH═CH$_2$, and —(CH$_2$)$_3$OC(O)C(CH$_3$)═CH$_2$.

11. The functional F-POSS of claim 8, wherein each of $R_1$ and $R_2$ is separately selected from the group consisting of —$CH_3$, —$(CH_2)_7CH_3$, —$C_6H_5$, —$CH=CH_2$, —$(CH_2)CH=CH_2$, —$(CH_2)_3OC(O)CH=CH_2$, and —$(CH_2)_3OC(O)C(CH_3)=CH_2$.

12. The functional F-POSS of claim 8, wherein each $R_f$ is separately selected from the group consisting of fluorotetradecyl, fluorododecyl, fluorodecyl, fluorooctyl, fluorohexyl, and hexafluoro-i-butyl.

\* \* \* \* \*